United States Patent [19]

Fahmy et al.

[11] 4,315,026

[45] Feb. 9, 1982

[54] ALKYLPOLYOXYSULFINYL AND ALKYLPOLYTHIOSULFINYL DERIVATIVES OF CARBAMATE ESTERS

[75] Inventors: Mohamed A. H. Fahmy, Edison, N.J.; Tetsuo R. Fukuto; Teruomi Jojima, both of Riverside, Calif.

[73] Assignee: The Regents of the University of California, Los Angeles, Calif.

[21] Appl. No.: 139,352

[22] Filed: Apr. 11, 1980

[51] Int. Cl.$^3$ .................... A01N 43/16; C07D 317/44
[52] U.S. Cl. .............................. 424/282; 260/340.5 R; 260/340.7; 260/340.9 R; 260/346.22; 260/346.73; 260/347.2; 260/456 A; 260/464; 260/465 D; 260/465.4; 424/180; 424/285; 424/300; 536/1; 536/115; 536/122; 549/33; 560/10; 560/11; 560/16; 560/17; 560/134; 560/135; 560/136; 560/137; 560/138; 560/148
[58] Field of Search ......... 260/465.4, 465 D, 340.5 R, 260/346.22, 340.7, 340.9 R; 560/10, 11, 16, 17, 148, 134, 135, 136, 137; 536/1, 115, 122; 424/282, 285, 300

[56] References Cited

U.S. PATENT DOCUMENTS

| | | | |
|---|---|---|---|
| 3,326,967 | 6/1967 | Ratz et al. | 560/137 |
| 3,663,594 | 5/1972 | Brown et al. | 560/10 X |
| 3,843,689 | 10/1974 | Brown et al. | 560/135 X |
| 3,914,259 | 10/1975 | Brown | 260/346.2 R |
| 4,262,015 | 4/1981 | Fahmy et al. | 260/340.9 R |
| 4,263,318 | 4/1981 | Fahmy et al. | 260/340.9 R |

FOREIGN PATENT DOCUMENTS

| | | | |
|---|---|---|---|
| 931467 | 7/1955 | Fed. Rep. of Germany | 560/137 |
| 1095806 | 6/1961 | Fed. Rep. of Germany | 560/137 |
| 497572 | 12/1938 | United Kingdom | 560/137 |

*Primary Examiner*—Ethel G. Love
*Attorney, Agent, or Firm*—Albert M. Herzig; Edward C. Walsh; Max Geldin

[57] ABSTRACT

A novel class of chemical compounds useful as pesticides consists of alkylpolyoxysulfinyl and alkylpolythiosulfinyl derivatives of carbamate esters. The preparation of these compounds and their formulation to control insects are exemplified.

40 Claims, No Drawings

ALKYLPOLYOXYSULFINYL AND ALKYLPOLYTHIOSULFINYL DERIVATIVES OF CARBAMATE ESTERS

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbofuran as effective pesticides.

U.S. Pat. No. 3,843,689 to Brown discloses production of N-methyl or N-phenyldithiocarbamates produced from N-chlorothiocarbamates, as insecticides.

In the copending application Ser. No. 18,598, filed Mar. 7, 1979, of Fahmy et al, now U.S. Pat. No. 4,263,318, a novel class of chemical compounds useful as pesticides, consisting of N-alkoxysulfinylcarbamate esters, and their method of preparation is described.

In the copending application, Ser. No. 18,417, filed Mar. 7, 1979, of Fahmy et al, now U.S. Pat. No. 4,262,015, a novel class of chemical compounds useful as pesticides, consisting of N-alkylthio- and N-arylthiosulfinyl-carbamate esters, and their method of preparation is disclosed.

The object of the present invention is to provide another novel class of carbamate ester compounds which are effective pesticides.

SUMMARY OF THE INVENTION

The novel carbamate ester compounds of the invention are generally alkylpolyoxysulfinyl and alkylpolythiosulfinyl derivatives of carbamate esters. The compounds are prepared by reacting an N-chlorosulfinyl-carbamate ester with a diol or dithiol, or with a polyol or polythiol in a suitable organic solvent such as tetrahydrofuran in the presence of a hydrogen chloride acceptor such as pyridine.

The resulting compounds of the invention are highly effective against certain pests and insects, and have substantially reduced mammalian toxicity, e.g. as compared to other potent insecticides such as carbofuran, described in U.S. Pat. No. 3,474,171. Thus, the invention compounds, while having high toxicity toward certain pests or insects, are relatively safe to mammals.

DETAILED DESCRIPTION OF THE INVENTION AND PREFERRED EMBODIMENTS

The sulfinylcarbamate esters or compounds of the invention have the formula noted below:

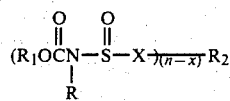

wherein R is methyl; $R_1$ is selected from the class consisting of a hydrocarbyl group containing from 1 to 20 carbon atoms, a 5 to 6 membered heterocyclic ring containing O or S atoms, and the $>C=N-$ group; $R_2$ is a hydrocarbyl group containing from 2 to 40 carbon atoms and derived from a compound selected from the group consisting of alkyl and aryl polyols, and alkyl and aryl polythiols, and which can contain unreacted hydroxyl or thiol groups, and protected hydroxyl or thiol groups; n is an integer of from 1 to 8; x is the number of unreacted hydroxyl or thiol groups, which can range from 0 to 7, and wherein n is greater than x; and X is O or S.

One or more of the hydroxyl or thiol groups in the compound of formula (2) can be appropriately protected, if desired. The term "protected" hydroxyl or thiol groups is defined hereinafter.

Thus, $R_1$ can be a hydrocarbyl group containing only hydrogen and carbon, and from 1 to 20 carbon atoms, preferably 1 to 12 carbon atoms, either aliphatic or aromatic, including substituted or unsubstituted alkyl cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio, dialkylamino and alkoxy groups; a 5 to 6 membered heterocyclic ring containing O or S atoms, e.g. benzothienyl, furanyl, benzofuranyl and 1,3-benzodioxolyl; or the $>C=N-$ group; the $>C=N-$ group can be represented more specifically by the formula:

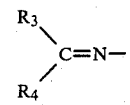

where $R_3$ is hydrogen, alkyl, alkylthio or cyano, and $R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where $R_1$ is aryl, preferred examples of such aryl groups are as follows:

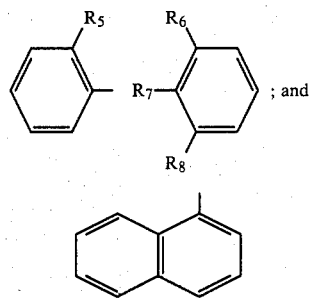

; and where $R_5$ is hydrogen, alkoxy, alkylthio, alkyl, alkylthioalkyl, 2-dioxalanyl or halogen, e.g. Cl or Br;

$R_6$ is alkyl, alkoxy, alkoxyalkyl or halogen;

$R_7$ is hydrogen, alkyl, halogen, alkylthio, alkoxy, dialkylamino or formyl(alkyl)amino;

$R_8$ is hydrogen or alkyl; and wherein the number of aliphatic carbon atoms in $R_3$, $R_4$, $R_5$, $R_6$, $R_7$ and $R_8$, individually should not exceed eight;

In one group of preferred carbamate ester compounds of the invention, $R_1$ is a hydrocarbyl group containing from 1 to 12 carbon atoms, either aliphatic or aromatic, including alkyl, e.g. methyl, ethyl, isopropyl, propyl, isobutyl, cycloalkyl, e.g. cyclohexyl, phenylalkyl, naphthylalkyl; aryl, e.g. phenyl, naphthyl, alkylphenyl, e.g. tolyl, xylyl, alkylnaphthyl, any of which can contain substituents such as halogen, e.g. chlorine or bromine, alkoxy, alkylthio and dialkylamino. Particularly preferred are those compounds where $R_1$ is alkylphenyl, e.g. 3-methylphenyl, and naphthyl groups, and which can be unsubstituted or substituted, e.g. with halogen, alkoxy, dialkylamino, alkylthio, alkylthioalkyl groups, and the like, and especially wherein $R_1$ is 3-alkylphenyl such as 3-isopropyl- and 3-secbutylphenyl, 2-alkoxyphenyl such as 2-isopropoxyphenyl, dialkylaminophenyl such as 3-methyl-4-dimethylamino and 3,5-dimethyl-4-dimethylaminophenyl, or 1-naphthyl. Particularly preferred also is the group of carbamate esters wherein $R_1$ is a heterocyclic ring, and including fused-on heterocyclic rings, containing one or two O or S atoms, and 5 to 6 members in the heterocyclic nucleus, e.g. benzofuranyl or 1,3-benzodioxolyl, and especially a 2,3-dihydrobenzofuranyl-7 group having the formula (3) below, and the 1,3-benzodioxol-4 group having the formula (4) below:

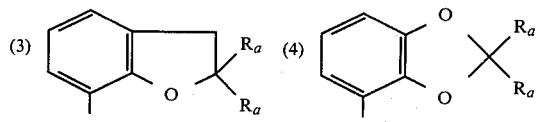

where $R_a$ is an alkyl group of 1 to about 4 carbon atoms, e.g. methyl, ethyl, propyl, n-butyl, and both $R_a$'s can be the same or different, and most preferably wherein $R_1$ is the 2,3-dihydro-2,2-dimethylbenzofuranyl-7 group or the 2,2-dimethyl-1,3-benzodioxol-4 group.

Another particularly preferred class of carbamates of the invention are those wherein $R_1$ is a group containing the $>C=N-$ radical, as defined above. Such $>C=N-$ groups can be, for example, the following:

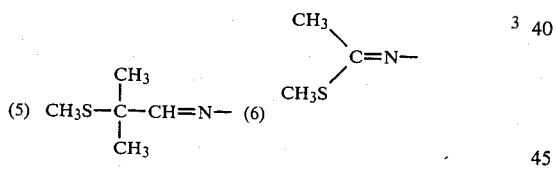

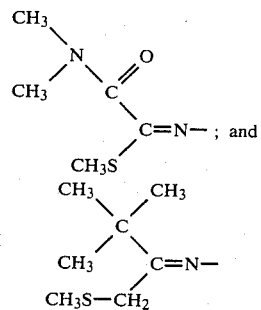

$R_2$ in all of the above preferred compounds is a hydrocarbyl group derived from diols and polyols, dithiols and polythiols, such as polyhydroxyalkanes, polyhydroxyaryls, and alkyl and arylpolythiols. Examples of such compounds are as follows:

1. Monomers of diols and triols, up to multiple hydroxyalkyl monomers, containing from 2 to 40 carbon atoms and up to 6 hydroxyl groups, e.g. 1,2-ethanediol, 1,3-propanediol, 1,2-propanediol, 2,4-butanediol, 1,5-butanediol, 1,6-hexanediol and the like; also triols such as glycerol (1,2,3-propanetriol), 1,2,6-hexanetriol, pentaerythrytol and the like; also, 2-phenyl-1,3-dioxane-5-ol, 2,2-dimethyl-1,3-dioxol-5-methanol, 3-allyloxy-1,2-propanediol, 2-allyloxy-1,3-propandiol, 3-benzyloxy-1,2-propanediol and 3-isopropoxy-1,2-propanediol; and also monosaccharides such as pentoses and hexoses, and α and β glucose and α and β fructose, with and without protecting groups.

2. Dimeric polyols and specifically disaccharides such as lactose and sucrose.

3. Dithiols and specifically 1,2-ethanedithiol, 1,2-propanedithiol, 1,4-butanedithiol and dithiols of the following structure $$HS-(CH_2)_2-X-(CH_2)_2-SH$$

wherein X is oxygen or sulfur.

The carbamate esters of the invention can be prepared by the following general reaction schemes: Reaction with diols and dithiols:

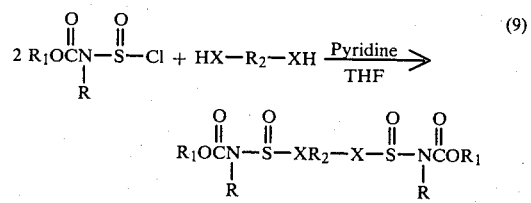

Reaction with polyols and polythiols:

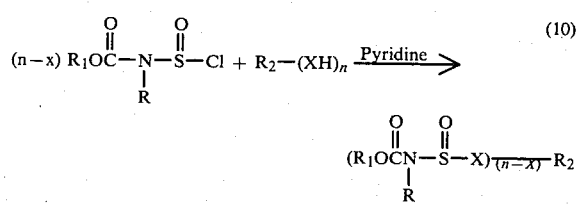

where R, $R_1$ and $R_2$ are as defined above, X is O or S, n equals the number of unprotected hydroxyl or thiol groups in the polyol or polythiol, and x is the number of unreacted hydroxyl or thiol groups in the final compound (n>x). Thus, n−x represents the number of available hydroxyl or thiol groups in the polyol or polythiol which are actually reacted with the carbamate ester. The term "polyols" and "polythiols" as employed here are meant to encompass compounds having at least two hydroxyl or at least two thiol groups or a combination of hydroxyls and thiols totaling at least two, and including diols and dithiols.

The hydroxyl or thiol groups in the above mentioned polyols and polythiols can be appropriately protected, if desired, before reacting with the chlorosulfinylcarbamate intermediates. The appropriate protecting groups include isopropylidene, unsubstituted or substituted benzylidene, such as benzylidene substituted with methyl or t-butyl in the benzylidene ring, alkyl, e.g. methyl, ethyl, propyl; alkenyl, e.g. allyl, alkinyl, e.g. propargyl; aralkyl, e.g. benzyl, acyl, e.g. acetyl, and halogenated acyl, e.g. chloroacetyl.

These protecting groups can be removed chemically from the final products, as by treatment with dilute acid, e.g. hydrochloric acid, or preferably, can be removed in a biological system so that the active toxicant is released.

In the above reaction, the N-chlorosulfinyl-carbamate ester intermediate is formed by the reaction of the corresponding carbamate with thionyl chloride, preferably using pyridine as hydrogen chloride acceptor in an inactive polar solvent such as tetrahydrofuran. Nonpolar solvents such as hexane also may be used. Such ester can be formed in high yield using essentially equivalent quantities of the carbamate and thionyl chloride and slightly more than an equivalent amount of pyridine. These novel intermediates and their method of production are described in the copending application Ser. No. 18,416, filed Mar. 7, 1979, by M. A. H. Fahmy and T. R. Fukuto, now U.S. Pat. No. 4,261,897.

Without isolation, the N-chlorosulfinylcarbamate ester intermediates can react in situ with diols or dithiols, or with polyols or polythiols, in the presence of an equivalent amount of pyridine as hydrogen chloride acceptor, e.g. to form alkylpolyoxysulfinyl and alkylpolythiosulfinyl derivatives of carbamate esters. The temperature of the reaction medium varies according to the reactivity of the diol or polyol, or the di- or polythiol. In general, the reaction can be carried out at temperatures from 10° to 60° C., e.g. ambient temperature, in an organic solvent such as dichloromethane, benzene, dimethylformamide or tetrahydrofuran.

It will be understood that if desired, the N-chlorosulfinylcarbamate ester starting material in reactions (9) and (10) above can be initially prepared and isolated as an intermediate compound, and such compound then reacted with the appropriate HX—R$_2$—XH or R$_2$—(XH)$_n$ compound as noted in the above reaction schemes.

The following examples are representative of the invention.

EXAMPLE I

Synthesis of N,N'-(1,2-ethanedioxysulfinyl)-bis (S-methyl N-methylcarbamoyloxy-thioacetimidate).

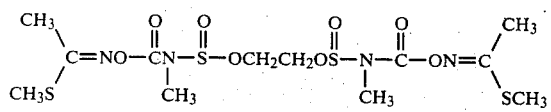

To a cold (5° C.) solution of S-methyl N'(methylcarbamoyloxy) thioacetimidate (6.6 g, 0.04 mol) and pyridine (4.0 g, 0.05 mol) in 40 ml dry tetrahydrofuran was added 5.0 g of thionyl chloride and the mixture was stirred for half an hour at 5° C. and for 6 hours at room temperature. Pyridine (4.0 g, 0.05 mol) was added and the mixture was cooled again to 5° C.

Ethylene glycol (1,2-dihydroxyethane, 1.5 g, 0.024 mol) was added dropwise while stirring. The temperature was allowed to rise up to room temperature and stirring was continued for an additional one hour. Dichloromethane (150 mol) was added and the mixture was washed with water three (30 ml each) times. The organic layer was dried over anhydrous sodium sulfate and the solvent was evaporated under vacuum. The product crystallized from ether mp 89°–92° C. NMR in chloroform-d-TMS showed the following absorptions:

δ4.35-4.2 (m, 4H, OCH$_2$CH$_2$O), 3.1 (s, 6H, di-NCH$_3$), 2.5 (s, 6H, di-N=CCH$_3$), 2.35 (s, 6H, di-SCH$_3$).

EXAMPLE II

Synthesis of N,N'-(1,3-Propanedioxysulfinyl)-bis (2,3-dihydro-2,2-dimethylbenzofuranyl-7 methylcarbamate)

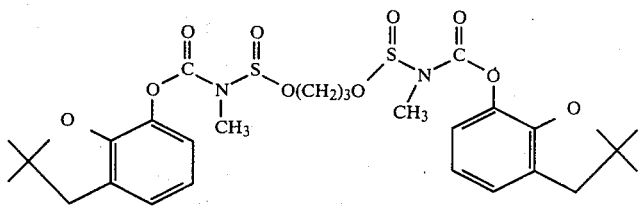

To a solution of 2,3-dihydro-2,2-dimethylbenzofuranyl-7 (chlorosulfinyl) (methyl) carbamate (0.02 mol) in tetrahydrofuran prepared from 2,3-dihydro-2,2-dimethylbenzofuranyl-7 methyl-carbamate and thionyl chloride as described in above copending U.S. application Ser. No. 18,416, was added pyridine (0.025 mol), followed by 1,3-propanediol (0.01 mol) in 5 ml tetrahydrofuran, dropwise at ice-water bath temperature.

The reaction mixture was diluted with 100 ml ether and worked up similar to Example I. The oily product obtained was further purified by preparative thin-layer chromatography. NMR of the purified product in chloroform-d-TMS showed the following absorptions: δ7.1-6.8 (m, 6H, aromatic protons), 4.3-4.1 (t. 4H, di-OCH$_2$), 3.1 (s, 6H, di—NCH$_3$), 3.0 (s, 4H, di-benzylic CH$_2$), 2.4-1.0 (m, 2H, aliphatic CH$_2$), 1.5 (s, 12H, di-gem-di-CH$_3$).

EXAMPLE III

Synthesis of S-methyl N-(2,2-dimethyl-1,3-dioxolane-5-yl-methoxysulfinyl)-N-methylcarbamoyloxythioacetimidate.

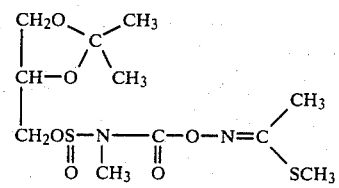

To a solution of S-methyl N-chlorosulfinyl-N-methylcarbamoyloxythioacetimidate (0.01 mol) in 10 ml of dry tetrahydrofuran as described in Example I was added pyridine (0.988 g, 0.0125 mol), followed by 2,2-dimethyl-1,3-dioxolane-5-methanol (1.32 g, 0.01 mol) in 2 ml tetrahydrofuran, dropwise at ice-water bath temperature.

After stirring the reaction mixture for 40 minutes at room temperature, it was diluted with 70 ml ether and worked up similar to Example I to give 2.7 g (80%) of crude product as a light brown solid. The solid was recrystallized from hexaneethyl acetate (3:1), giving 1.64 g of pure material, m.p. 72°–74° C. (colorless needles). NMR(CDCl$_3$-TMS): δ3.6-4.3

(m, 5H, —CH₂ĊHCH₂—), 3.0 (s, 3H, N—CH₃), 2.37 (s, 3H, N=C—CH₃), 2.27 (s, 3H, S—CH₃), 1.35 (d, C(CH₃)₂).

EXAMPLE IV

Synthesis of N,N',N''-(1,2,3-propanetrioxysulfinyl) tris-(3-methylphenyl methylcarbamate).

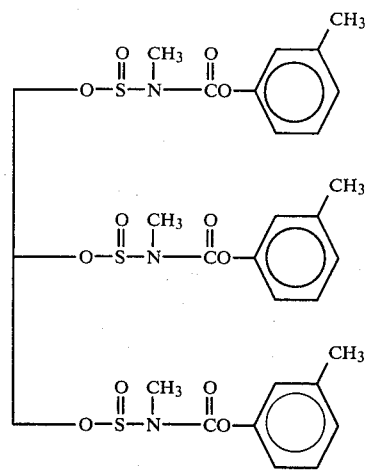

To a solution of 3-methylphenyl N-chlorosulfinyl-N-methylcarbamate prepared from 3-methylphenyl methylcarbamate (1.65 g, 0.01 mol), pyridine (0.988 g, 0.0125 mol), thionyl chloride (1.25 g, 0.0105 mol) and anhydrous tetrahydrofuran (10 ml) as described in Example I was added pyridine (0.0125 mol), followed by glycerol (0.31 g, 0.003 mol) in dry dimethylformamide (2 ml) dropwise and the reaction mixture was stirred for 50 minutes at room temperature. Working up as described in Example III gave 2 g (83%) of crude product as a yellow oil. The oil was purified by silicic acid column chromatography using benzene and benzene-ethyl acetate (10:1) as eluting solvents to give 1.25 g (38%) of pure material, n$_D^{24}$ 1.5525 (light yellow oil). NMR (CDCl₃-TMS): δ6.8–7.3 (m, 12H, aromatic protons), 4.77 (quintet, 1H,

—CH₂ĊHCH₂—), 3.9–4.4 (m, 4H,

—CH₂—ĊH—CH₂—), 3.08 (s, 9H, N—CH₃), 2.33 (s, 9H, CH₃).

EXAMPLE V

Synthesis of S-methyl N-(1,2,5,6-di-O-isopropylidene-3-O-glucofuranosylsulfinyl)-N-methylcarbamoyloxythioacetimidate.

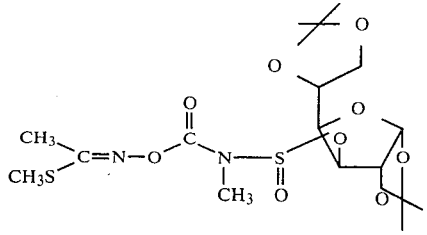

To a solution of S-methyl N-chlorosulfinyl-N-methylcarbamoyloxythioacetimidate (0.01 mol) in 10 ml of dry tetrahydrofuran prepared as described in Example I was added pyridine (0.0125 mol), followed by 1,2,5,6-diisopropylidene-δ-glucose (2.6 g, 0.01 mol) in tetrahydrofuran (5 ml) dropwise at ice-water bath temperature. The reaction mixture was stirred for 40 minutes at room temperature. Working up as described in Example I gave 3.12 g (67%) of crude product as a brown solid. Recrystallization of the solid from hexaneethyl acetate gave 1.06 g (23%) of pure material, m.p. 141° C. (colorless prisms). NMR (CDCl₃-TMS): δ5.88 (d, 1H, 1-H), 4.77 (d, 1H, 3-H), 4.58 (d, 1H, 2—H), 3.8–4.4 (m, 4H, protons at 4,5 and 6-positions), 3.07 (s, 3H, N-CH₃), 2.40 (s, 3H, N=C-CH₃), 2.27 (s, 3H, S—CH₃), 1.50, 1.40, 1.30, 1.27 (each s, total 12H, CH₃×4).

EXAMPLE VI

Synthesis of S-methyl N-(1,2,4,5-di-O-isopropylidene 3-O-fructopyranosylsulfinyl)-N-methylcarbamoyloxy-2-(N',N'-dimethylamino)-2-oxoethanimidothioate.

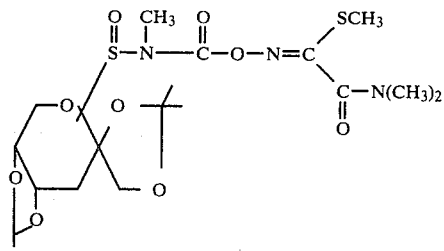

To a solution of S-methyl N-chlorosulfinyl-N-methylcarbamoyloxy-2-(N',N'-dimethylamino)-2-oxoethanimidothioate prepared from S-methyl N-methylcarbamoyloxy-2-(N',N'-dimethylamino)-2-oxoethanimidothioate (2.19 g, 0.01 mol), pyridine (0.988 g, 0.0125 mol), thionyl chloride (1.25 g, 0.0105 mol) and anhydrous tetrahydrofuran (10 ml) as described in Example I was added pyridine (0.0125 mol), followed by 1,2,4,5-di-O-isopropylidene-α-fructose (2.6 g, 0.01 mol) in tetrahydrofuran (4 ml), dropwise at ice-cold temperature. The reaction mixture was stirred for 30 minutes at room temperature. Working up as described in Example I gave 5.87 g (112%) of crude product as a yellow oil. The oil was purified by preparative thin-layer chromatography (silicic acid) using ethyl acetate as a developing solvent to give 1.3 g (25%) of pure material, m.p. 55°–57° (colorless prisms). NMR (CDCl₃—TMS): δ3.8–4.4 (m, 7H, fructose protons), 3.08 (s, 3H, N—CH₃), 3.07 (s, 6H, N(CH₃)₂, 2.33 (s, 3H, S—CH₃), 1.52, 1.43, 1.37, 1.33 (each s, total 12H, CH₃×4).

EXAMPLE VII

Synthesis of N,N',N'',N''',N''''-(α-glucosylsulfinyl)-pentakis (2,3-dihydro-2,2-dimethylbenzofuranyl-7 methyl-carbamate).

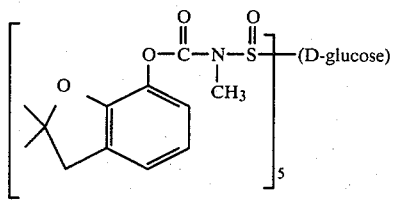

To a solution of 2,3-dihydro-2,2-dimethylbenzofuranyl-7 methylcarbamate (13.2 g, 0.06 mol) in benzene (100 ml) was added pyridine (6.0 g, 0.075 mol) and thionyl chloride (7.5 g, 0.063 mol) and the mixture was stirred at room temperature for 24 hours. Pyridine hydrochloride was filtered rapidly and the benzene solution was concentrated to about 25 ml by means of a water aspirator.

Anhydrous D-glucose (1.8 g, 0.01 mol) was dissolved in 100 ml anhydrous pyridine and the solution was chilled in the ice-box. To this solution was added the above benzene solution and the mixture was shaken frequently at about 0° C. for 3 hours. The mixture was let stand at room temperature for 7 hours, and was poured over 500 ml ice-water mixture. This solution was extracted with 250 ml dichloromethane and the organic layer was dried over anhydrous sodium sulfate, and then evaporated under vacuum. The residue was dissolved in 50 ml benzene and the unreacted carbamate was crystallized out, and filtered. The benzene solution was evaporated again and the residue was subjected to high vacuum resulting in a glassy type material.

NMR of this product in chloroform-d-TMS showed the following absorptions: δ7.2–6,6 15H, aromatic protons, 4.7–4.0 (broad multiplet, 7H, the sugar CH), 3.2–2.9 (m, 25H, 5-NCH$_3$ and 5 benzylic CH$_2$), 1.4 (s, 30H, 5 gem-di-CH$_3$).

EXAMPLE VIII

Synthesis of N,N'-(1,2-Ethanedithiosulfinyl)-bis (S-methyl N-methylcarbamoyloxy thioacetimidate)

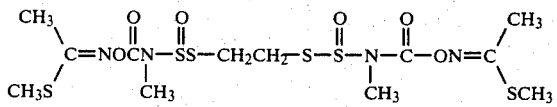

To a solution of S-methyl N-(N'-methylcarbamoyloxy) thioacetimidate (6.6 g, 0.04 mol) in 40 ml tetrahydrofuran was added pyridine (4.0 g, 0.05 mol) and the mixture was stirred in an ice-water bath. To this solution was added thionyl chloride (5.0 g, 0.042 mol), and the mixture was stirred at room temperature for 5 hours. Pyridine (4.0 g, 0.05 mol) was added and the mixture was cooled again in an ice-water bath. 1,2-Ethanedithiol (1.9 g, 0.02 mol) in 5 ml tetrahydrofuran was added dropwise over a period of 15 minutes. The reaction mixture was stirred at room temperature for one half hour and worked up with dichloromethane as described in Example I. The product crystallized from dichloromethane-hexane mixture to give 8.6 g (85% yield), mp. 125°–127° C. NMR of product in chloroform-d-TMS gave the following absorptions: δ3.35 (3, 4H, 2 SCH$_2$), 3.15 (s, 6H, 2 NCH$_3$), 2.45 (s, 6H, N=CCH$_3$), 2.3 (s, 6H, 2 SCH$_3$).

EXAMPLE IX

Synthesis of N,N'-(1,2-Ethanedithiosulfinyl)-bis (2,3-dihydro-2,2-dimethyl-benzofuranyl-7)methylcarbamate)

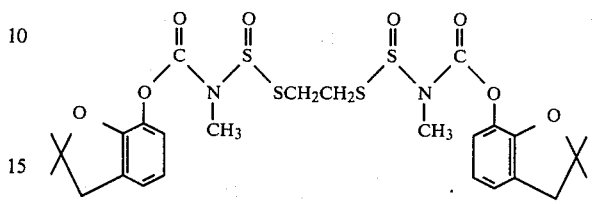

To a solution of 2,3-dihydro-2,2-dimethylbenzofuranyl-7 (chlorosulfinyl) (methyl)carbamate (0.02 mol) prepared from 4.4 g of 2,3-dihydro-2,2-dimethylbenzofuranyl-7 methylcarbamate and thionyl chloride in tetrahydrofuran as described in above U.S. application Ser. No. 18,416, was added pyridine (2.0 g, 0.025 mol) and 1,2-ethanedithiol (1.0 g, 0.01 mol) as described in Example VIII. Workup of the reaction mixture as described in Example I resulted in a highly viscous product. Purification of a sample of this product using preparative thin-layer chromatography and ethyl acetate-hexane mixture (1:2) as the developing solvent resulted in a product which showed the required absorptions by NMR spectrometry in chloroform-d-TMS, as follows: δ7.1–6.65 (m, 6H, aromatic protons), 3.4 (s, 4H, 2 SCH$_2$), 3.15 (s, 6H, 2 NCH$_3$), 3.0 (s, 4H, 2 benzylic CH$_2$), 1.5 (s, 12H, 2 gem-dimethyl).

The following are additional examples of the carbamate esters of the invention:

X  S-Methyl N-(2-phenyl-1,3-dioxane-5-ylmethoxysulfinyl)N-methylcarbamoyloxythioacetimidate XI  N,N'-(3-Allyloxy-1,2-propanedioxysulfinyl)-bis (S-methyl N-methylcarbamoyloxythioacetimidate)

XII  N,N'-(2-Allyloxy-1,3-propanedioxysulfinyl)-bis (S-methyl N-methylcarbamoyloxythioacetimidate)

XIII  N,N'-(3-Benzyloxy-1,2-propanedioxysulfinyl)-bis (S-methyl N-methylcarbamoyloxythioacetimidate)

XIV  N,N'-(3-Isopropoxy-1,2-propanedioxysulfinyl)-bis (S-methyl N-methylcarbamoyloxythioacetimidate)

XV  N,N',N'',-(1,2,3-Propanetrioxysulfinyl)-tris (S-methyl N-methylcarbamoyloxythioacetimidate)

XVI  S-Methyl N-(2,3,4,5-di-O-isopropylidene-1-α-O-fructopyranosylsulfinyl)-N-methylcarbamoyloxythioacetimidate XVII  S-Methyl N-(1,2,4,5-di-O-isopropylidene-3-O-fructopyranosylsulfinyl)-N-methylcarbamoyloxythioacetimidate XVIII  3-Methylphenyl N-(2-phenyl-1,3-dioxane-5-ylmethoxysulfinyl)-N-methylcarbamate XIX  N,N'-(3-Allyloxy-1,2-propanedioxysulfinyl)-bis (3-methylphenyl methylcarbamate)

XX  3-Methylphenyl N-(2,2-dimethyl-1,3-dioxolane-5-ylmethoxysulfinyl)-N-methylcarbamate XXI  N,N'-(2-Allyloxy-1,3-propanedioxysulfinyl)-bis (3-methylphenyl methylcarbamate)

XXII  N,N'-(3-Benzyloxy-1,2-propanedioxysulfinyl)-bis (3-methylphenyl methylcarbamate)

XXIII  N,N'-(3-Isopropoxy-1,2-propanedioxysulfinyl)-bis (3-methyl-phenyl methylcarbamate)

XXIV  3-Methylphenyl N-(2,3,4,5-di-O-isopropylidene-1-α-O-fructopyranosylsulfinyl)-N-methylcarbamate XXV 3-Methylphenyl N-(1,2,4,5-di-O-isopropylidene-3-O-fructopyranosylsulfinyl)-N-methylcarbamate XXVI 3-Methylphenyl N-(1,2,5,6-di-O-isopropylidene-3-O-glucofuranosylsulfinyl)-N-methylcarbamate XXVII S-Methyl N-(2-phenyl-1,3-dioxane-5-ylmethoxysulfinyl)-N-methylcarbamoyloxy-2-(N',N'-dimethylamino)-2-oxoethanimidothioate XXVIII S-Methyl N-(2,2-dimethyl-1,3-dioxolane-5-ylmethoxysulfinyl)-N-methylcarbamoyloxy-2-(N'N'-dimethylamino)-2-oxoethanimidothioate XXIX N,N'-(3-Allyloxy-1,2-propanedioxysulfinyl)-bis[S-methyl N-methylcarbamoyloxy-2-(N',N'-dimethylamino)-2-oxoethanimidothioate]

XXX N,N'-(2-Allyloxy-1,3-propanedioxysulfinyl)-bis-[S-methyl N-methylcarbamoyloxy-2-(N',N'-dimethylamino)-2-oxoethanimidothioate]

XXXI N,N'-(3-Benzyloxy-1,2-propanedioxysulfinyl)-bis-[S-methyl carbamoyloxy-2-(N',N'-dimethylamino)-2-oxoethanimidothioate]

XXXII N,N'-(3-Isopropoxy-1,2-propanedioxysulfinyl)-bis[S-methyl N-methylcarbamoyloxy-2-(N',N'-dimethylamino)-2-oxoethanimidothioate]

XXXIII N,N',N''-(1,2,3-Propanetrioxysulfinyl)-tris-[S-methyl N-methylcarbamoyloxy-2-(N',N'-dimethylamino)-2-oxoethanimidothioate]

XXXIV S-Methyl N-(2,3,4,5-Di-O-isopropylidene-1-α-O-fructopyranosylsulfinyl)-N-methylcarbamoyloxy-2-(N',N'-dimethylamino)-2-oxoethanimidothioate XXXV S-Methyl N-(1,2,5,6-di-O-isopropylidene-3-O-glucofuranosylsulfinyl) N-methylcarbamoyloxy-2-(N',N'-dimethylamino)-2-oxoethanimidothioate XXXVI N,N'-(3-Allyloxy-1,2-propanedioxysulfinyl)-bis(1-naphthyl methylcarbamate)

XXXVII N,N'-(2-Allyloxy-1,3-propanedioxysulfinyl)-bis(1-naphthyl methylcarbamate)

XXXVIII N,N'-(3-Benzyloxy-1,2-propanedioxysulfinyl)-bis(1-naphthyl methylcarbamate)

XXXIX N,N'-(3-Isopropoxy-1,2-propanedioxysulfinyl)-bis(1-naphthyl methylcarbamate)

XL N,N',N''-(1,2,3-Propanetrioxysulfinyl)-tris-(1-naphthyl methylcarbamate)

XLI 1-Naphthyl N-(2,3,4,5-di-O-isopropylidene-1-α-O-fructopyranosylsulfinyl)-N-methylcarbamate XLII 1-Naphthyl N-(1,2,4,5-di-O-isopropylidene-3-α-O-fructopyranosylsulfinyl)-N-methylcarbamate XLIII N,N',N''(1,2,3-Propanetrioxysulfinyl)-tris-(2-isopropoxyphenyl methylcarbamate)

XLIV 2-Isopropoxyphenyl N-(2,3,4,5-di-O-isopropylidene-1-α-O-fructopyranosylsulfinyl)-N-methylcarbamate The insecticidal alkylpolyoxysulfinyl and alkylpolythiosulfinyl derivatives of carbamate esters of the invention may be formulated with the usual carriers, including additives and extenders used in the preparation of insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays, and other known solid carriers used in the insecticide art. These concentrates are compositions containing about 5 to about 95% toxicant and the rest inert material which includes dispersing agents, emulsifying agents, and wetting agents. The concentrates are diluted for practical application, with water or other liquid sprays or with additional solid carrier for application as a dust or granular formulation.

The concentration of the toxicant in the dilution generally used for application is normally in the range of about 10% down to about 0.001%, depending on the means available for application. Many variations of spraying and dusting compositions in the art may be used, by substituting a compound of this invention into compositions known or apparent to the art.

The present compounds may also be made into compositions which may be applied without further dilution, for example, dusts, powders and granules. These ready to use formulations generally contain from about 0.1% to 50% of the toxicant, preferably about 1.0 to about 45%.

The insecticidal compositions may be formulated and applied with other active ingredients, including other insecticides, nematicides, acaricides, fungicides, plant regulators, fertilizers, etc. In applying chemicals, it is obvious that an effective amount and concentration of the carbamate ester compounds of the invention should be employed.

BIOLOGICAL ACTIVITY

Representative compounds of the alkylpolyoxysulfinyl and alkylpolythiosulfinyl derivatives of carbamate esters of the invention were tested for insecticidal activity against house flies, Musca domestica.

In one series of tests for house flies, the test compound was dissolved in acetone to a concentration of 1%. All of the invention compounds tested and listed in Table I below gave a 100% kill of a population of female house flies treated with 1 µl of this solution by topical application.

For mice toxicity, the compound was dissolved in propyleneglycol or corn oil as a carrier and all compounds were tested at the level up to 1,000 mg/kg. All of the above noted compounds tested were lower in toxicity as compared with the parent compounds.

In another series of tests, stock 1% concentrated solutions of each of the test compounds of Table I below, and of the commercial related carbamate ester insecticides methomyl, carbofuran and oxamyl, were made in acetone, and such solutions were diluted with acetone to a concentration of 0.001–0.8%. House flies were treated topically on the notum by 1 µl of each of the diluted acetone solutions and percent mortality was counted 24 hours after application. Insects were held at a constant temperature of 60° F. Results are presented as $LD_{50}$ in µg/g for house flies.

Mammalian toxicity was determined against Swiss white mice. The test compound was applied orally using propylene glycol as the carrier. Results are given as $LD_{50}$ in mg of compound per kg body weight. The toxicological data for a number of typical esters of the invention are summarized in Tables I and II.

The term "$LD_{50}$" represents the dose needed to kill 50% of the test animals. In interpreting the values in the tables below, the lower the value for $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

TABLE I

Toxicity of the Carbamate Esters of the Invention and Certain Common Insecticides Against House Flies and White Mice Common structure (Examples I, III, VIII, XI, XII, XIII, XIV, XVI, XVII):

$$R\left[-\underset{\underset{CH_3}{|}}{N}-\underset{\underset{O}{\|}}{C}-O-N=C\underset{SCH_3}{\overset{CH_3}{\diagup}}\right]_n$$

| Compound of Example | R | n | House flies LD$_{50}$ (µg/g) | Mice LD$_{50}$ (mg/kg) |
|---|---|---|---|---|
| | H (methomyl) | 1 | 3.7 | 10 |
| I | CH$_2$OS(O)— / CH$_2$OS(O)— (linked) | 2 | 60 | 52 |
| III | (pinacol-type bicyclic diol derivative with —OS(O)—) | 1 | 7 | 84 |
| VIII | CH$_2$S—S(O)— / CH$_2$S—S(O)— | 2 | 75 | 250 |
| XI | —OS(O)— / —OS(O)— / —OCH$_2$CH=CH$_2$ | 2 | 40 | 50–80 |
| XII | CH$_2$=CHCH$_2$O—C(—OS(O)—)(—OS(O)—) | 2 | <50 | 88 |
| XIII | —OS(O)— / —OS(O)— / —OCH$_2$—C$_6$H$_5$ | 2 | <50 | 50–100 |
| XIV | —OS(O)— / —OS(O)— / —O—CH(CH$_3$)$_2$ | 2 | 81.5 | 170 |
| XVI | (diacetone sugar derivative with —OS(O)—) | 1 | 50 | 500 |
| XVII | (diacetone sugar derivative with —S(O)—) | 1 | 115 | 1000 |

Common structure (Examples II):

$$R\left[-\underset{\underset{CH_3}{|}}{N}-\underset{\underset{O}{\|}}{C}-O-\text{(benzofuranyl)}\right]_n$$

| Compound of Example | R | n | House flies LD$_{50}$ (µg/g) | Mice LD$_{50}$ (mg/kg) |
|---|---|---|---|---|
| | H (carbofuran) | 1 | 6.7 | 2 |
| II | —OS(O)— / —OS(O)— | 2 | 17 | 92 |

TABLE I-continued
Toxicity of the Carbamate Esters of the Invention and Certain Common Insecticides Against House Flies and White Mice $$R \left[ \begin{array}{c} CH_3 \\ | \\ N \end{array} \begin{array}{c} O \\ || \\ C \end{array} - O - N = C \begin{array}{c} CN(CH_3)_2 \\ || \\ O \end{array} \right]_n$$
$$\phantom{xxxxxxxxxxxxxxxxxxxxxxxxxxxxxx} SCH_3$$

| Compound of Example | R | n | House flies LD$_{50}$ ($\mu$g/g) | Mice LD$_{50}$ (mg/kg) |
|---|---|---|---|---|
| IX | CH$_2$SS(O)— <br> \| <br> CH$_2$SS(O)— | 2 | 36 | 87 |
| | H (oxamyl) | 1 | 3.6 | 3.7 |
| XXVII | (phenyl-dioxolane)–OS(O)— | 1 | 161 | 25 |
| XXVIII | (isopropylidene dioxolane)–OS(O)— | 1 | 2.6 | 31 |
| XXIX | —OS(O)— <br> —OS(O)— <br> —OCH$_2$CH=CH$_2$ | 2 | 215 | 12.5–25 |
| XXXIV | (diacetone sugar)–OS(O)— | 1 | 20 | 44 |
| XXXV | (diacetone sugar)–S(O)— | 1 | 26.5 | 25–50 |

TABLE II
Toxicity of the Carbamate Esters of the Invention Against White Mice

| Compound of Example | Mice LD$_{50}$ (mg/kg) |
|---|---|
| X | 85 |
| XV | 50–100 |
| XVIII | >1,000 |
| XIX | >1,000 |
| XX | >1,000 |
| XXI | >1,000 |
| XXII | >1,000 |
| XXIII | >1,000 |
| XXIV | >1,000 |
| XXV | >1,000 |
| XXVI | >1,000 |
| XXXI | 12.5–25 |
| XXXII | 16 |
| XXXVI | >1,000 |
| XXXVII | >1,000 |
| XXXVIII | >1,000 |
| XXXIX | >1,000 |
| XXXX | >1,000 |
| XXXXI | >1,000 |
| XXXXII | >1,000 |
| XXXXIII | >1,000 |
| XXXXIV | >1,000 |

The relatively low values for the various compounds of the invention listed in Table I for LD$_{50}$ for house flies indicates good toxicity of the invention compounds as against such insects, although some of them are not as potent in this respect as the parent carbamate ester insecticides Methomyl, Carbofuran and Oxamyl. However, and of particular significance, the mammalian toxicity of the invention compounds of Tables I and II above, as indicated by their high $LD_{50}$ values for mice, is from 5 to 100 times lower as compared with the corresponding values for the parent carbamate ester insecticide. Thus, the above Tables I and II show that the carbamate esters of the invention have good insecticidal activity or potency, but have substantially reduced mammalian toxicity or substantially greater mammalian safety.

As previously noted, the hydroxyl or thiol groups of the compounds of the invention can carry protecting or blocking groups, as illustrated by the isopropylidene protecting groups in the compounds of Examples III, V and VI. These compounds can function as insecticides, and also as systemic nematicides. By blocking off the hydroxyl or thiol groups with suitable substituents, this enables the compounds to be absorbed by the plant, and once within the plant the protecting groups are removed, forming hydroxyl or thiol groups. This changes the physical properties of the compound to more polar compounds, permitting the compounds to be carried down to the root zone, to kill nematodes.

While we have described particular embodiments of the invention for purposes of illustration, it will be understood that various changes and modifications within the spirit of the invention can be made, and the invention is not to be taken as limited except by the scope of the appended claims.

What is claimed is:

1. Carbamate esters having pesticidal activity selected from the class having the formula:

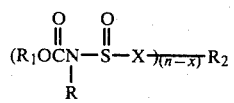

where R is methyl; $R_1$ is selected from the class consisting of a hydrocarbyl group containing from 1 to 20 carbon atoms, a 5 to 6 membered heterocyclic ring containing one to two O or S atoms, the remaining ring atoms being carbon atoms, and the group

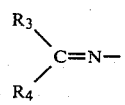

where
$R_3$ is hydrogen, alkyl, alkylthio or cyano, and
$R_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl, or alkoxy groups, the number of aliphatic carbon atoms in $R_3$ and $R_4$ not exceeding eight; $R_2$ is hydrocarbyl group containing from 2 to 40 carbon atoms and derived from a compound selected from the group consisting of alkyl and aryl polyols, and alkyl and aryl polythiols, and which can contain unreacted hydroxyl groups or thiol groups, and protected hydroxyl or thiol groups, wherein the protecting groups are selected from the class consisting of isopropylidene, benzylidene, alkenyl, alkinyl, aralkyl, acyl, and halogenated acyl; n is an integer of from 1 to 8; x is the number of unreacted hydroxyl or thiol groups which can range from 0 to 7, and where n is greater than x; and X is O or S; provided that when (n-x)=1, $R_2$ shall contain at least one unreacted hydroxyl or thiol group, or at least one of said protected hydroxyl or thiol groups.

2. Carbamates as defined in claim 1, wherein $R_1$ is an aryl group selected from the class consisting of:

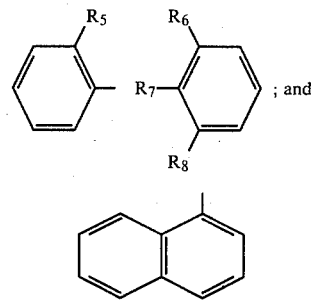

where $R_5$ is hydrogen, alkoxy, alkylthio, alkyl, alkylthioalkyl, 2-dioxolanyl, or halogen;
$R_6$ is alkyl, alkoxy, alkoxyalkyl, or halogen;
$R_7$ is hydrogen, alkyl, halogen, alkylthio, alkoxy, dialkylamino or formyl(alkyl)amino; and
$R_8$ is hydrogen or alkyl; the number of aliphatic carbon atoms in $R_5$, $R_6$, $R_7$, and $R_8$, individually, not exceeding eight.

3. Carbamates as defined in claim 2, wherein $R_1$ is:

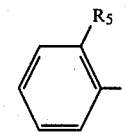

4. Carbamates as defined in claim 2, wherein $R_1$ is:

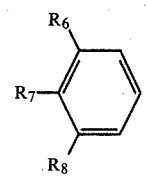

5. Carbamates as defined in claim 1, wherein $R_1$ is 1-naphthyl.

6. Carbamates as defined in claim 1, where $R_1$ is a 5 to 6 membered heterocyclic ring containing one or two O to S atoms, the remaining ring atoms being carbon atoms.

7. Carbamates as defined in claim 1, wherein some of the hydroxyl or thiol groups are protected with said protecting groups.

8. Carbamates as defined in claim 1, wherein $R_2$ is a hydrocarbyl group derived from a compound selected from the group consisting of (a) monomers of diols and triols, and hydroxyalkyl monomers containing from 2 to 40 carbon atoms and up to 6 hydroxyl groups, (b) dimeric polyols, and (c) dithiols of the structure $$HS-(CH_2)_2-X-(CH_2)_2-SH$$

where X is oxygen or sulfur.

9. Carbamates as defined in claim 8, wherein $R_2$ is derived from a compound selected from the group consisting of alkane diols, alkane triols and monosaccharides.

10. Carbamate esters having pesticidal activity selected from the class having the formula:

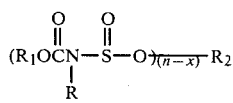

where R is methyl; $R_1$ is selected from the class consisting of a hydrocarbyl group containing from 1 to 20 carbon atoms, a 5 to 6 membered heterocyclic ring containing one to two O or S atoms, the remaining ring atoms being carbon atoms, and the group

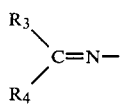

where
$R_3$ is hydrogen, alkyl, alkylthio or cyano, and
$R_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl or alkoxy groups, the number of aliphatic carbon atoms in $R_3$ and $R_4$ not exceeding eight; $R_2$ is hydrocarbyl group containing from 2 to 40 carbon atoms and derived from a compound selected from the group consisting of alkyl and aryl polyols, and which can contain unreacted hydroxyl groups and protected hydroxyl groups, wherein the protecting groups are selected from the class consisting of isopropylidene, benzylidene, alkenyl, alkinyl, aralkyl, acyl, and halogenated acyl; n is an integer of from 1 to 8; x is the number of unreacted hydroxyl groups which can range from 0 to 7, and where n is greater than x; provided that when (n-x)=1; $R_2$ shall contain at least one unreacted hydroxyl group or at least one of said protected hydroxyl groups.

11. Carbamates as defined in claim 10, wherein $R_2$ is derived from a monosaccharide selected from the group consisting of glucose and fructose, with and without protecting groups.

12. Carbamates as defined in claim 10, wherein $R_2$ is derived from a compound selected from the group consisting of lactose and sucrose.

13. Carbamates as defined in claim 8, wherein $R_2$ is derived from a dithiol of the structure

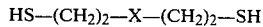

where X is oxygen or sulfur.

14. Carbamates as defined in claim 8, wherein $R_2$ is derived from a compound selected from the group consisting of ethylene glycol, glucose and 1,2-ethanedithiol.

15. Carbamates as defined in claim 1, where $R_1$ is a hydrocarbyl group containing from 1 to 12 carbon atoms.

16. Carbamates as defined in claim 1, wherein $R_1$ is an aryl group selected from the group consisting of phenyl and naphthyl.

17. Carbamates as defined in claim 16, wherein said aryl group can be substituted with one or more halogen, cyano, nitro, alkyl, alkylthio, dialkylamino, and alkoxy groups.

18. Carbamates as defined in claim 16, wherein $R_1$ is selected from the group consisting of 3-isopropylphenyl 3-secbutylphenyl, 2-isopropoxyphenyl, 3-methylphenyl, 3-methyl 4-dimethyl-aminophenyl, and 3,5-dimethyl-4-dimethylaminophenyl.

19. Carbamates as defined in claim 1, wherein $R_1$ is a heterocyclic ring containing one to two O or S atoms, and 5 to 6 members in the heterocyclic nucleus, the remaining ring atoms being carbon atoms.

20. Carbamates as defined in claim 1, wherein X is sulfur.

21. Carbamates as defined in claim 19, wherein $R_1$ is a benzofuranyl or a 1,3-benzodioxolyl group.

22. Carbamates as defined in claim 1, wherein $R_1$ is selected from the class having the formulae:

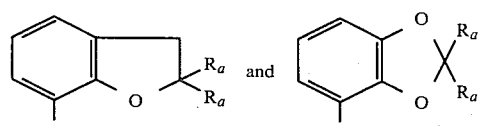

where $R_a$ is an alkyl group of 1 to about 4 carbon atoms, and both $R_a$'s can be the same or different.

23. Carbamates as defined in claim 1, wherein $R_1$ is the 2,3-dihydro-2,2-dimethylbenzofuranyl-7 group, or the 2,2-methyl-1,3-benzodioxol-4 group. 1,3-benzodioxol-4 group.

24. Carbamates as defined in claim 1, wherein $R_1$ is selected from the class having the formulae:

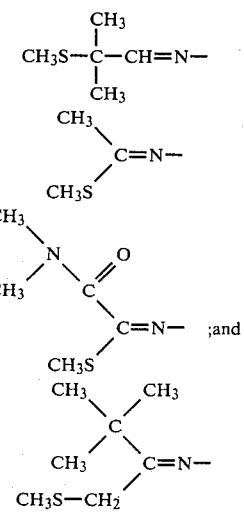

;and

25. Carbamates as defined in claim 24, wherein $R_1$ is the group having the formula:

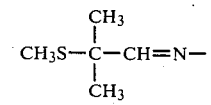

26. Carbamates as defined in claim 1, wherein $R_2$ is derived from a compound selected from the class consisting of 1,2-ethanediol, 1,3-propanediol, 1,2-propanediol, 2,4-butanediol, 1,5-butanediol, 1,6-hexanediol, glycerol and 1,2,6-hexanetriol, 2-phenyl-1,3- dioxane-5-ol, 2,2-dimethyl-1,3-dioxol-5-methanol, 3-allyloxy-1,2-propanediol, 2-allyloxy-1,3-propanediol, 2-benzyloxy-1,2-propanediol and 3-isopropoxy-1,2-propanediol.

27. Carbamate as defined in claim 10, which is N,N'-(1,2-ethanedioxylsulfinyl)-bis(S-methyl N-methylcarbamoyloxy thioacetimidate.

28. Carbamate as defined in claim 10, which is N,N'-(1,3-propanedioxysulfinyl)-bis(2,3-dihydro-2,2-dimethylbenzofuranyl -7 methylcarbamate).

29. Carbamate as defined in claim 1, which is S-methyl N(2,2-dimethyl-1,3-dioxolane-5-yl-methoxysulfinyl)-N-methylcarbamoyloxy thioacetimidate.

30. Carbamate as defined in claim 10, which is N,N',N''-(1,2,3-propanetrioxysulfinyl)-tris(3-methylphenyl methylcarbamate).

31. Carbamate as defined in claim 10, which is S-methyl N-(1,2,5,6-di-O-isopropylidene-3-O-glucofuranosylsulfinyl)-N-methylcarbamoyloxy thioacetimidate.

32. An insecticidal composition comprising an insecticidally effective amount of a carbamate as defined in claim 1, in admixture with a carrier.

33. An insecticidal composition comprising an insecticidally effective amount of a carbamate as defined in claim 2, in admixture with a carrier.

34. An insecticidal composition comprising an insecticidally effective amount of a carbamate as defined in claim 10, in admixture with a carrier.

35. An insecticidal composition comprising an insecticidally effective amount of a carbamate as defined in claim 22, in admixture with a carrier.

36. An insecticidal composition comprising an insecticidally effective amount of a carbamate as defined in claim 24, in admixture with a carrier.

37. The method of controlling insects which comprises applying to the sites of infestation an insecticidally effective amount of a compound as defined in claim 1.

38. The method of controlling insects which comprises applying to the sites of infestation an insecticidally effective amount of a compound as defined in claim 10.

39. The method of controlling insects which comprises applying to the sites of infestation an insecticidally effective amount of a compound as defined in claim 23.

40. The method of controlling insects which comprises applying to the sites of infestation an insecticidally effective amount of a compound as defined in claim 25.

* * * * *